(12) United States Patent
Dibiasi et al.

(10) Patent No.: US 11,797,933 B2
(45) Date of Patent: *Oct. 24, 2023

(54) HEALTHCARE DEBIT CARD LINKED TO HEALTHCARE-RELATED AND NON-HEALTHCARE-RELATED FINANCIAL ACCOUNTS

(71) Applicant: Alegeus Technologies, LLC, Waltham, MA (US)

(72) Inventors: John P. Dibiasi, Sedona, AZ (US); Douglas L. Norman, Brookfield, WI (US); Jimmie L. Lindsey, Milwaukee, WI (US)

(73) Assignee: ALEGEUS TECHNOLOGIES, LLC, Waltham, MA (US)

( * ) Notice: Subject to any disclaimer, the term of this patent is extended or adjusted under 35 U.S.C. 154(b) by 99 days.

This patent is subject to a terminal disclaimer.

(21) Appl. No.: 17/334,061

(22) Filed: May 28, 2021

(65) Prior Publication Data
US 2021/0398076 A1    Dec. 23, 2021

Related U.S. Application Data

(63) Continuation of application No. 16/533,161, filed on Aug. 6, 2019, now Pat. No. 11,023,857, which is a
(Continued)

(51) Int. Cl.
*G06Q 10/10*    (2023.01)
*G06Q 40/08*    (2012.01)
(Continued)

(52) U.S. Cl.
CPC ............. *G06Q 10/10* (2013.01); *G06Q 20/10* (2013.01); *G06Q 20/34* (2013.01); *G06Q 40/02* (2013.01);
(Continued)

(58) Field of Classification Search
CPC ....... G06Q 40/08; G06Q 10/10; G06F 19/328
See application file for complete search history.

(56) References Cited

U.S. PATENT DOCUMENTS 6,000,608 A    12/1999    Dorf
7,380,707 B1 *  6/2008    Fredman ................ G06Q 10/10
                                                              235/375
(Continued)

OTHER PUBLICATIONS

V. Gogou, S. Pavlopoulos, D. Karayiannis and D. Koutsouris, "A smart card network in health care services," Proceedings of the 22nd Annual International Conference of the IEEE Engineering in Medicine and Biology Society (Cat. No. 00CH37143), Chicago, IL, USA, 2000, pp. 559-561 vol.1, doi: 10.1109/IEMBS (Year: 2000).*
(Continued)

*Primary Examiner* — Joseph D Burgess
(74) *Attorney, Agent, or Firm* — Foley & Lardner LLP

(57) ABSTRACT

A healthcare financial payment system and method are disclosed in which a debit card which may be used by a cardholder to pay for medical products and services is linked with a healthcare-related financial account associated with the cardholder as well as with a non-healthcare-related financial account belonging to the cardholder. The healthcare-related financial account associated with the cardholder may be a Flexible Spending Arrangement (FSA), a Health Savings Account (HSA), or a health reimbursement arrangement (HRA), and the non-healthcare-related financial account associated with the cardholder may be a bank checking or savings account or a credit card. Any expenses for medical goods and services which are not covered by the cardholder's medical insurance may be paid from the cardholder's healthcare-related financial account if the medical goods or services are eligible and if there are funds remaining in the healthcare-related financial account, with any
(Continued)

remaining costs being paid for from or charged to the cardholder's non-healthcare-related financial account.

20 Claims, 5 Drawing Sheets

Related U.S. Application Data continuation of application No. 14/751,876, filed on Jun. 26, 2015, now Pat. No. 10,417,627, which is a continuation of application No. 11/364,514, filed on Feb. 28, 2006, now abandoned.

(51) Int. Cl.
    *G16H 40/20*     (2018.01)
    *G06Q 40/02*     (2023.01)
    *G16H 10/65*     (2018.01)
    *G06Q 20/10*     (2012.01)
    *G06Q 20/34*     (2012.01)

(52) U.S. Cl.
    CPC ............ *G06Q 40/08* (2013.01); *G16H 10/65* (2018.01); *G16H 40/20* (2018.01)

(56) References Cited

U.S. PATENT DOCUMENTS

| | | |
|---|---|---|
| 7,594,611 B1 | 9/2009 | Arrington, III |
| 2005/0080692 A1 | 4/2005 | Padam et al. |
| 2005/0177050 A1 | 8/2005 | Cohen |
| 2005/0288964 A1 | 12/2005 | Lutzen et al. |
| 2006/0064380 A1 | 3/2006 | Zukerman |
| 2006/0149670 A1* | 7/2006 | Nguyen ................. G06Q 20/40 705/39 |
| 2007/0007335 A1* | 1/2007 | Cracchiolo ............ G06Q 40/00 235/380 |
| 2009/0048954 A1 | 2/2009 | Blackburn et al. |
| 2014/0304010 A1* | 10/2014 | Kennedy ................ G06Q 40/08 705/4 |

OTHER PUBLICATIONS

Final Office Action on U.S. Appl. No. 14/751,876, dated Dec. 4, 2018.
Non-Final Office Action on U.S. Appl. No. 16/533,161 dated Sep. 25, 2020.
Notice of Allowance on U.S. Appl. No. 14/751,876 dated May 20, 2019.
Notice of Allowance on U.S. Appl. No. 16/533,161 dated Feb. 11, 2021.
U.S. Office Action on U.S. Appl. No. 11/364,514, dated Mar. 26, 2015.
U.S. Office Action on U.S. Appl. No. 14/751,876, dated Jan. 18, 2018.
U.S. Office Action on U.S. Appl. No. 14/751,876, dated May 25, 2018.
U.S. Office Action on U.S. Appl. No. 14/751,876, dated Aug. 9, 2017.

* cited by examiner

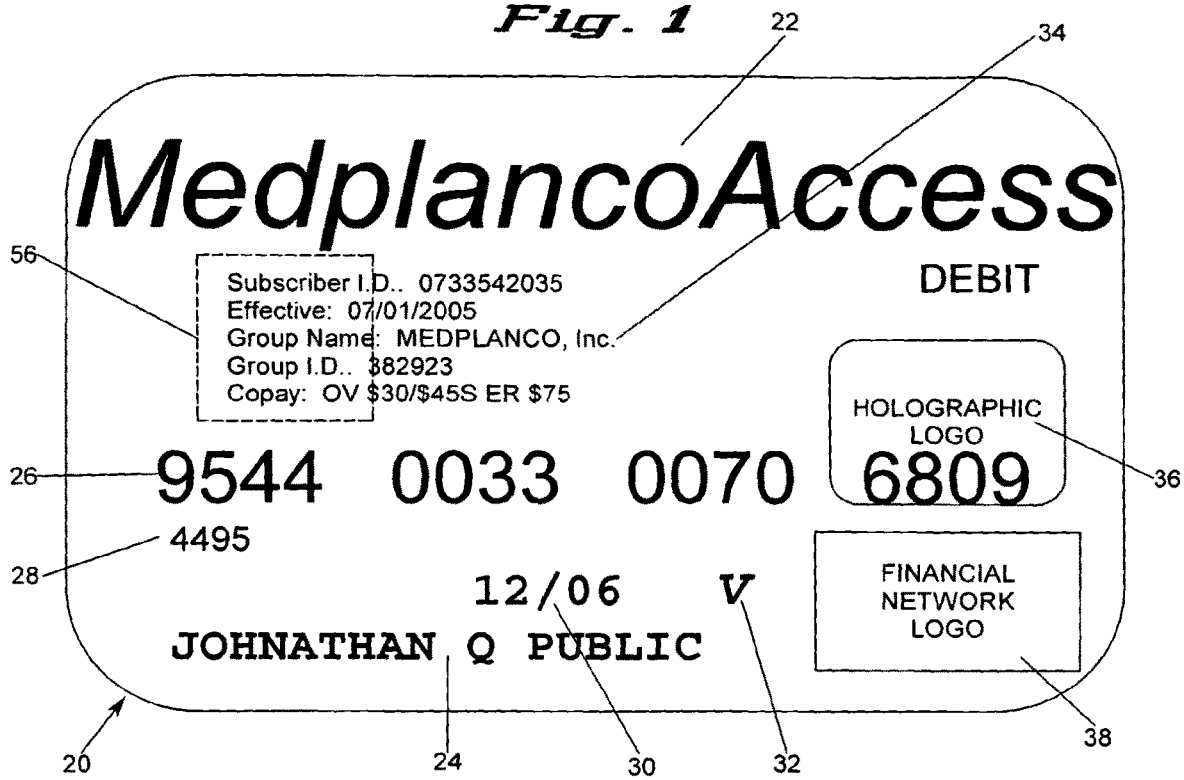
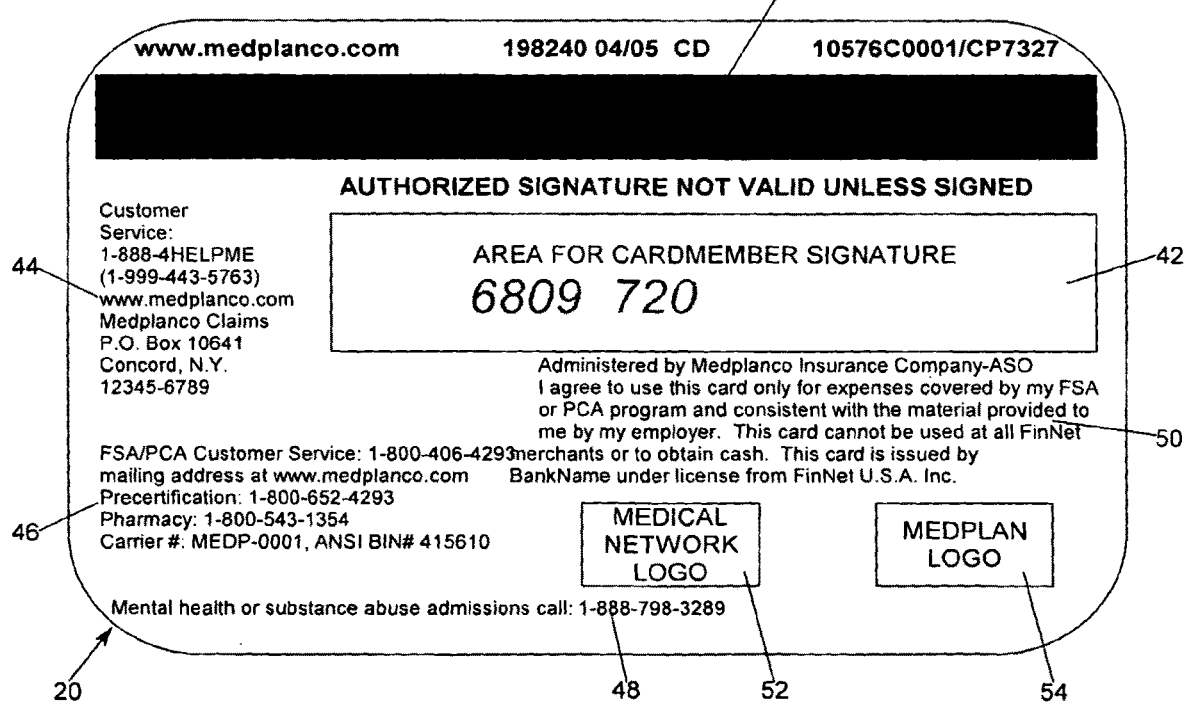

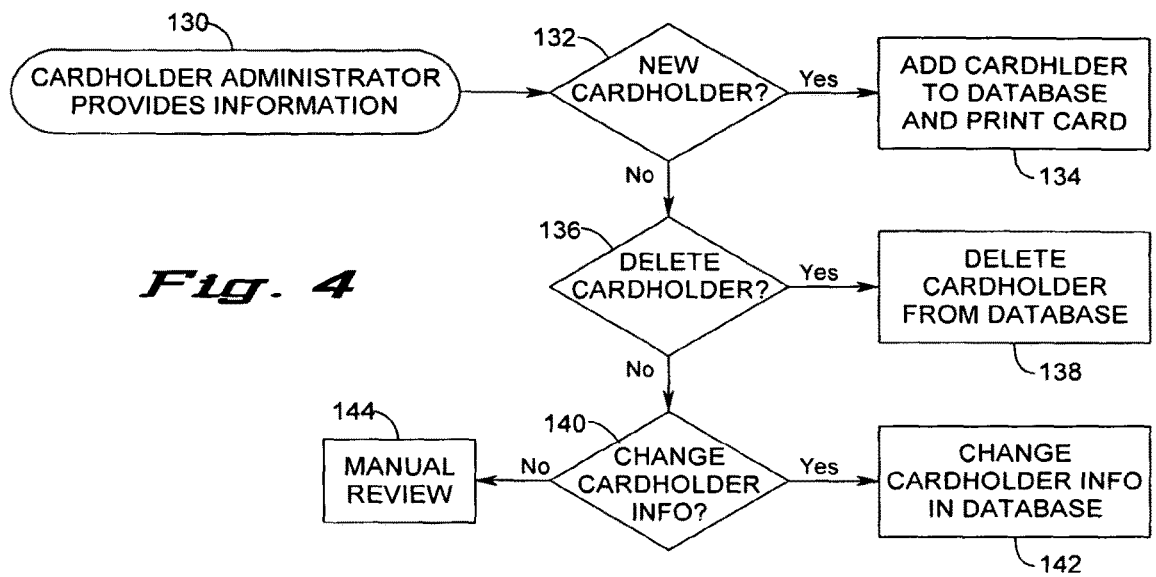
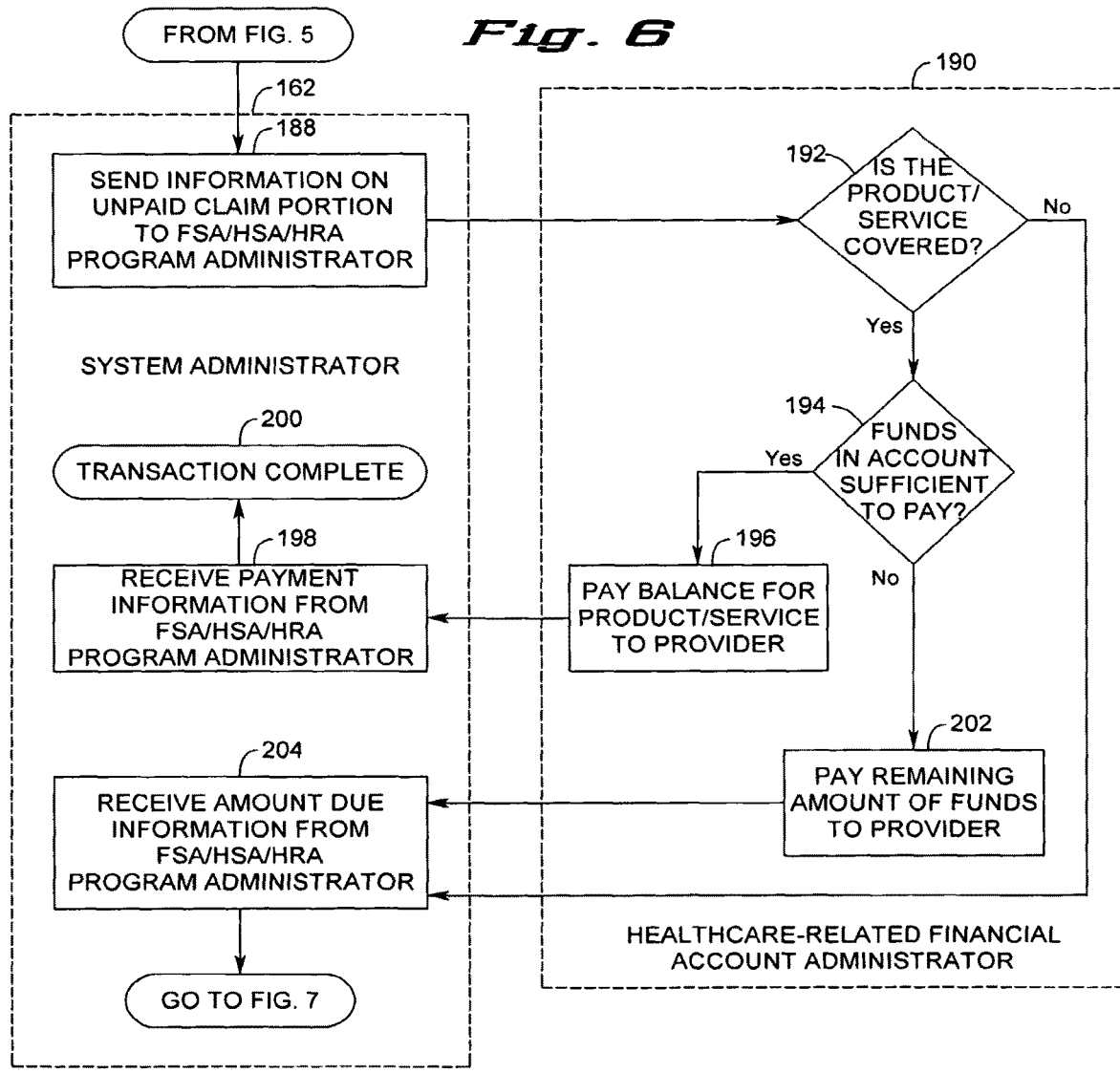

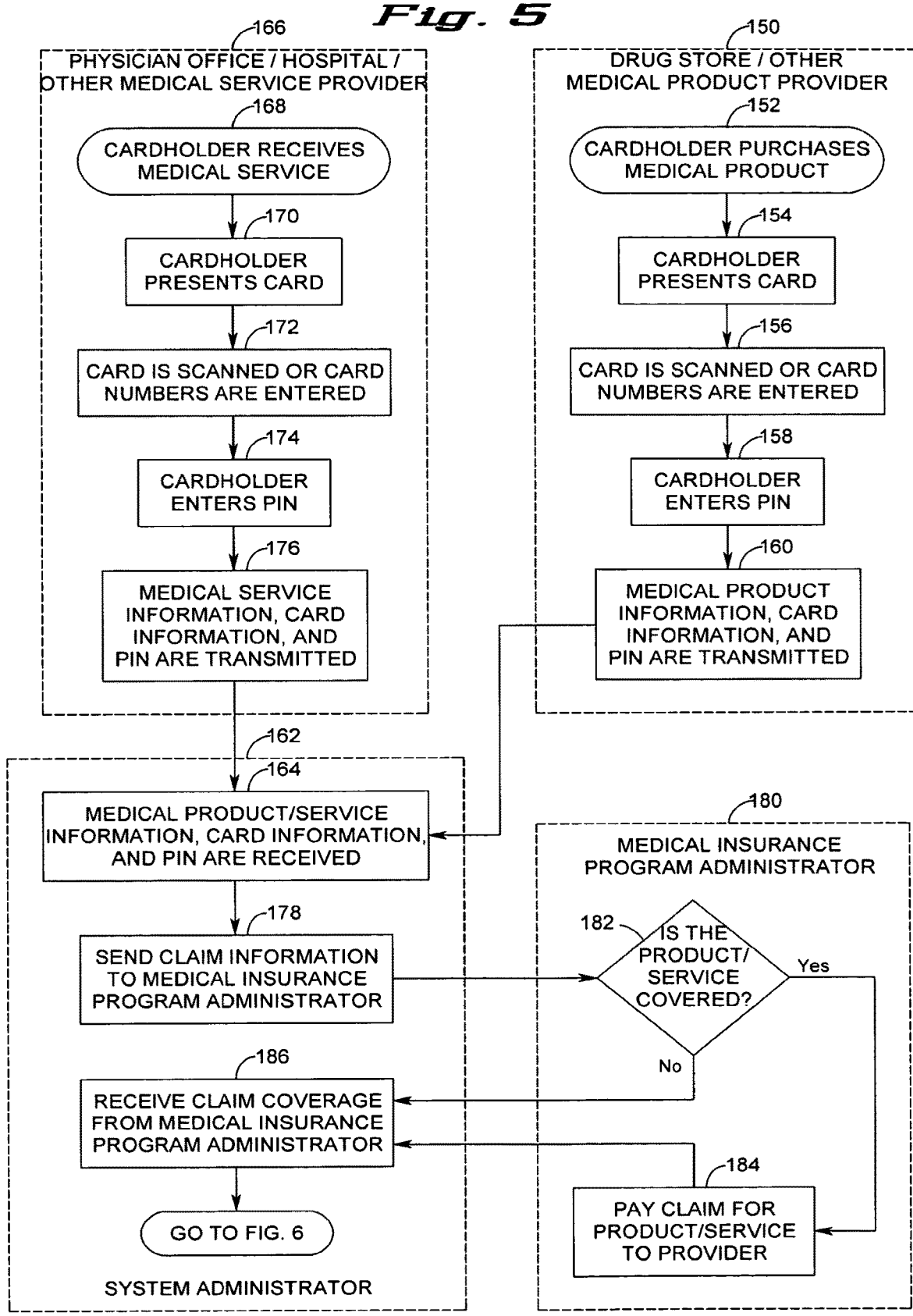

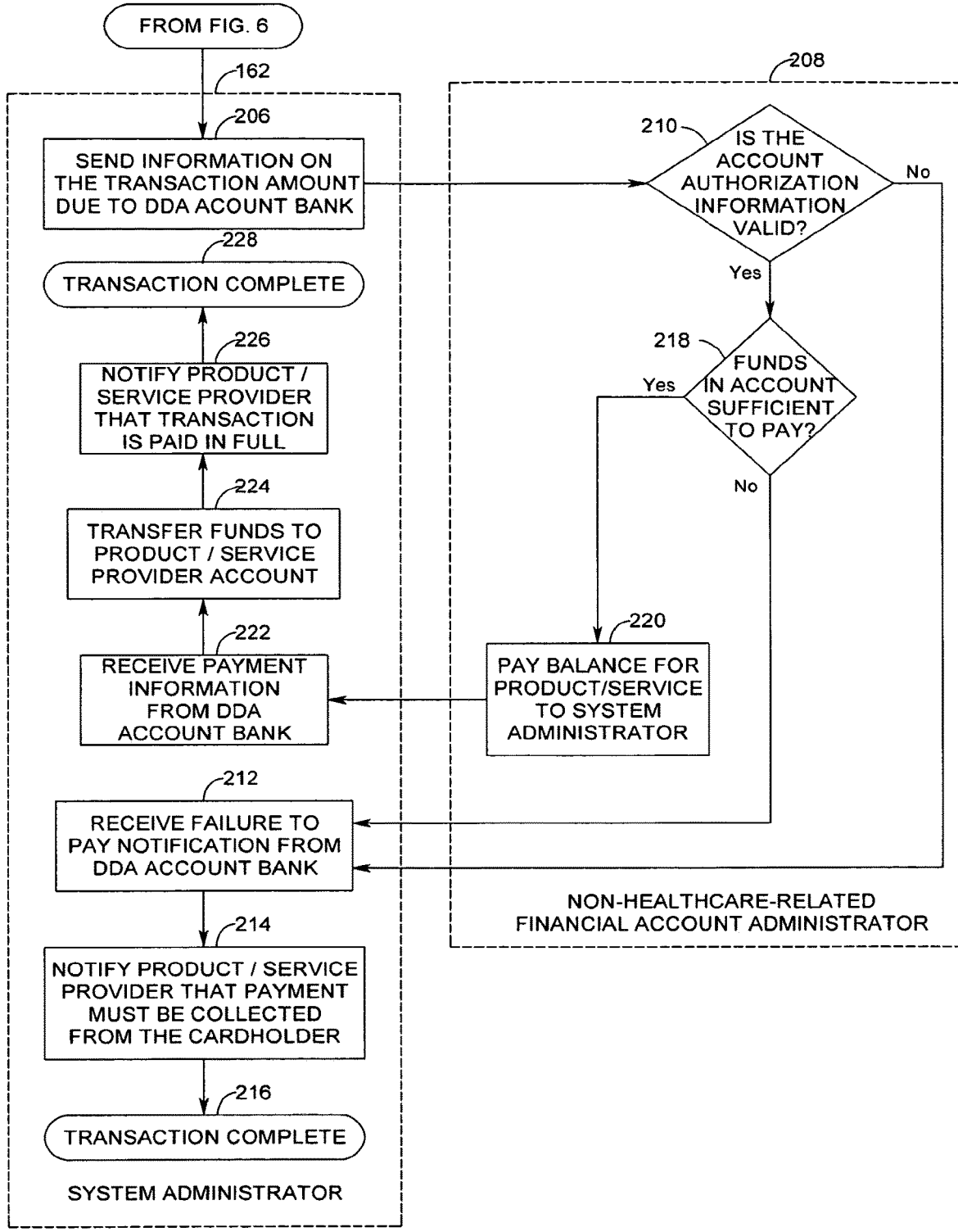

HEALTHCARE DEBIT CARD LINKED TO HEALTHCARE-RELATED AND NON-HEALTHCARE-RELATED FINANCIAL ACCOUNTS

CROSS-REFERENCE TO RELATED APPLICATIONS

This application claims the benefit of priority under 35 U.S.C. § 120 as a continuation of U.S. patent application Ser. No. 16/533,161, filed Aug. 6, 2019, which claims the benefit of priority under 35 U.S.C. § 120 as a continuation of Ser. No. 14/751,876, filed Jun. 26, 2015, which claims the benefit of priority under 35 U.S.C. § 120 as a continuation of Ser. No. 11/364,514, filed Feb. 28, 2006, each of which is hereby incorporated by reference herein in its entirety.

BACKGROUND OF THE INVENTION

Field of the Invention

The present invention relates generally to healthcare financial payment systems and methods, and more particularly to a novel system and method in which a healthcare debit card used by a cardholder to pay for medical products and services is linked with a healthcare-related financial account associated with the cardholder as well as with a non-healthcare-related financial account belonging to the cardholder.

With the widespread use of medical insurance has come the necessity of establishing that a particular individual has medical insurance coverage and arranging for the payment of medical products and services which are provided to the individual. At physicians' offices, hospitals, and pharmacies, the established policy has become that unless proof of coverage is provided at the time of provision of medical services or purchase of medical products, the consumer must pay, or make arrangements to pay, for the cost of the medical products or services at the time of their delivery. At physicians' offices at the time of service, consumers having medical insurance are typically required to present a card evidencing proof of the consumer's medical insurance plan and information regarding the plan including the copay amount required for an office visit, and pay the copay amount.

At hospitals, consumers having medical insurance typically present the card evidencing proof of the consumer's medical insurance plan and information regarding the plan prior to delivery of medical services (other than in the case of an emergency). At pharmacies, consumers having medical insurance are required to present the card evidencing proof of the consumer's medical insurance plan and information regarding the plan including the copay amount required for the prescription(s) being obtained, and pay the copay amount. In each of these situations, the consumer is required to either pay a copay amount prior to the delivery of medical services or a prescription, or, in the case of a hospital, to agree to pay the hospital for the amount which is not covered by the consumer's medical insurance.

This system of payment for medical services and products operated as described above until federal laws were passed to allow a participant and eligible dependents to save a considerable amount of money in taxes through a Flexible Spending Arrangement ("FSA"). FSA programs allow participants to deduct a predetermined amount of money from the participant's before-tax income. This predetermined amount of money is set aside in the participant's healthcare-related financial account, which is sometimes referred to as a flexible spending account or a flex account. The money then can be used toward paying for expenses incurred for certain eligible products and services specified by the IRS. Because the money is deducted from the employee's before-tax income through payroll deductions, the amount of tax that is actually paid by the employee is reduced. Further, the employer's FICA payment is reduced based on the applicable amount of pre-tax contributions made by their employees. As FSA plan is not portable.

A Health Savings Account ("HSA") is a tax-advantaged trust or custodial healthcare-related financial account created for the benefit of an individual (not limited to employees) who is covered under a high deductible health plan ("HDHP"). The HSA provider need not require proof of HDHP coverage but may desire to do so for purposes of its recordkeeping and reporting. If an employer sets up an HSA for an employee, however, the employer must verify that the employee is enrolled in an HDHP offered by the employer. Contributions may be made by an employer, the individual, or a family member (subject to the gift tax). Contributions are deductible if made by an individual and are excludable from income and wages if they are made by an employer. Earnings grow tax-free and distributions for qualified medical expenses are tax-free. Nonqualified withdrawals are subject to income and penalty taxes, and excess contributions are subject to a six percent excise tax. Like an IRA, the HSA is owned by the individual and is portable.

A health reimbursement arrangement ("HRA") is an arrangement funded solely by an employer. An HRA may be offered to employees or former employees. Amounts in the HRA healthcare-related financial account must be used for qualified medical expenses, and balances may be carried forward. Depending upon the terms of the HRA, coverage may (or may not) continue if the employee terminates service. An HRA is not portable.

The operation of a healthcare provider in conjunction with such healthcare-related financial accounts (any of an FSA, an HSA, or an HRA) typically involves three entities which each have a predefined function. The first of these entities is a cardholder administrator that enrolls employees or other cardholders serviced by a particular healthcare program. The cardholder administrator, in the process of enrolling employees or cardholders, obtains information from the employees or cardholders and their dependants and provides that information to the second and third entities.

The second entity is a medical insurance program administrator that administers the claims of cardholders under the medical insurance of the healthcare program. The medical insurance program administrator typically establishes payment schedules and deductibles for medical products and services and informs providers of such medical products and services of the amounts which will they be paid by the medical insurance portion of the healthcare program. The medical insurance program administrator also typically provides healthcare cards to the employees or cardholders, which they can present to providers of medical products and services as proof of enrollment in the medical insurance program.

The third entity is a healthcare-related financial account administrator, which administers the healthcare-related financial accounts which are owned by the employees or cardholders. The healthcare-related financial account administrator reviews the eligibility of medical products and services which are submitted by employees or cardholders in order to determine whether the medical products and services are eligible for payment from the healthcare-related financial accounts. If the medical products and services are eligible, the healthcare-related financial account administrator then determines whether the cardholders have sufficient funds left in their healthcare-related financial accounts. If the medical product or services in question are eligible, and if there are sufficient funds, the healthcare-related financial account administrator sends payment, typically to the employee or cardholder.

In all healthcare systems involving medical insurance, whether or not the employees or cardholders have healthcare-related financial accounts, the cardholders generally complete each transaction involving obtaining medical products or services by paying a remaining amount directly to the medical product or service providers. Additionally, in many healthcare systems there is uncertainty about the final cost to the employee or cardholder since the approval and payment systems do not operate in real time. Finally, since there is no central coordination of the various aspects of the healthcare program, each of the entities often operates without any interaction with the other entities.

It is accordingly the primary objective of the present invention that it provide a system and method for linking a healthcare debit card to both a healthcare-related financial account and a non-healthcare-related financial account in addition to linking the healthcare debit card to a medical insurance program. It is a related objective of the present invention that the healthcare debit card contain sufficient information, either in printed form or in electronic form, or in both forms, to enable medical product and service providers to ascertain that the healthcare debit card provides for payment from the three sources. It is another related objective of the present invention that it be capable of working which any of a plurality of different healthcare-related financial accounts, including FSA, HSA, and HRA healthcare-related financial accounts.

It is an additional objective of the present invention that it provide coordination between the submissions for payment of medical products and services to a medical insurance provider, the healthcare-related financial account, and the non-healthcare-related financial account to ensure that the submissions to these three entities are made quickly and in the proper sequence. It is a related objective that the system and method of the present invention be capable of operation in real time or in near-real time, thereby enabling complete resolution of payment for the medical products and services at the time of delivery. It is a further objective that the healthcare debit card used in the system and method of the present invention may optionally be used as a conventional credit or debit card for use in purchasing non-medical products and services.

The system and method of the present invention must also be flexible of design and robust in operation, and once established it should require little or no effort to maintain it other than to keep the employee or cardholder data current. In order to enhance the market appeal of the system of the present invention, it should also be relatively inexpensive to implement and to operate to thereby give it a high perceived value-to-cost ratio to afford it the broadest possible market. Finally, it is also an objective that all of the aforesaid advantages and objectives of the system and method of the present invention be achieved without incurring any substantial relative disadvantage.

SUMMARY OF THE INVENTION

The disadvantages and limitations of the background art discussed above are overcome by the present invention. With this invention, a healthcare debit card is provided which has the cardholder's name, a healthcare debit card number, and healthcare plan information typically including deductible amounts printed thereon. The healthcare debit card also has a magnetic stripe used to store data including information about the card, the cardholder, a healthcare plan, and financial account information on the back side of the healthcare debit card. Alternately, the healthcare debit card may instead be a standard size card which contains an electronic chip which may be used to store the same type of information. Such cards, commonly referred to as "smartcards," have a built-in microprocessor and memory used for identification and/or financial transactions.

The system of the present invention is used to link the healthcare debit card to a medical insurance provider and to a healthcare-related financial account, as well as to a non-healthcare-related financial account. The healthcare-related financial account may be a Flexible Spending Arrangement (FSA), a Health Savings Account (HSA), or a Health Reimbursement Arrangement (HRA). The non-healthcare-related financial account may be a bank checking or savings account or a credit card, or any other type of non-healthcare-related financial account.

The system of the present invention links together a number of entities which each have a predefined function in the operation of the system. The first entity is a cardholder administrator that enrolls employees or other cardholders serviced by a particular healthcare program. The function of the cardholder administrator is to provide information regarding cardholders to the system, typically by entering that information into a computer terminal. The second entity is a medical insurance program administrator that administers the claims of cardholders under the medical insurance of the healthcare program. These two entities have existed historically, and the medical insurance program administrator has informed providers of medical products and services of the amounts which will be paid by the medical insurance of the healthcare program.

A third entity is a healthcare-related financial account administrator, which administers healthcare-related financial accounts which are owned by cardholders. The healthcare-related financial account can be any one of a Flexible Spending Arrangement (FSA), a Health Savings Account (HSA), or a Health Reimbursement Arrangement (HRA). This entity has also existed historically, and the healthcare-related financial account administrator has reviewed the eligibility of medical products and services which are submitted by cardholders in order to determine whether the medical products and services are eligible for payment from the healthcare-related financial accounts. If they are eligible, the healthcare-related financial account administrator then pays for them if the cardholders have sufficient funds left in their healthcare-related financial accounts.

The system and method of the present invention adds two additional entities, and also provides a mechanism for medical product and service providers to obtain essentially instant payment for all medical products and services. The first additional entity may be a financial institution in which a cardholder has a financial account, which may for example be any of a conventional checking or savings account or a credit card. The second additional entity is a system administrator, which serves to coordinate the operations performed under the system and method of the present invention between all of the other entities.

In addition, each of the medical product and service providers is provided with a system interface to allow them to electronically communicate with the other entities in the system. This may be coordinated through the system administrator, or the interfaces of each of the entities may be configured to communicate with each other to the extent necessary and/or desirable. In the preferred embodiment, each of the medical product or service providers utilizes a facility terminal having a card reader to read the data stored on the healthcare debit card so that it may be transmitted to the various entities in the system that need the data. In the embodiment discussed herein, the communication between the various entities and providers may be provided by the Internet. Alternately, some or all of the network links between the various entities could be private networks as well.

In operation, a cardholder presents the healthcare debit card to a medical product or service provider. The healthcare debit card is scanned and information relating to the medical product or service together with the data from the healthcare debit card is provided to the system of the present invention. The medical insurance program administrator reviews the information relating to the medical product or service and the data from the healthcare debit card and determines whether the medical product or service is covered and what the deductible amount is. Information relating to coverage and the remaining amount which is due for the medical product or service is then provided by the medical insurance program administrator to the system of the present invention.

Next, the healthcare-related financial account administrator reviews the information relating to the medical product or service, the data from the healthcare debit card, and the remaining amount which is due for the medical product or service and determines whether the medical product or service is covered and whether the cardholder has sufficient funds in the healthcare-related financial account. Information relating to eligibility, payment of the remaining amount which is due for the medical product or service, and any resulting remaining amount due for the medical product or service is provided by the healthcare-related financial account administrator to the system of the present invention.

If there is any remaining unpaid amount, the non-healthcare-related financial account administrator (which may be a DDA deposit bank or a credit card administrator) determines whether the cardholder has sufficient funds in the DDA deposit account or on the credit card. If there are sufficient funds in the non-healthcare-related financial account, the remaining amount due for the medical product or service is taken from the non-healthcare-related financial account, and the medical product or service provider is notified that the medical product or service is paid for. If there are not sufficient funds in the non-healthcare-related financial account, the medical product or service provider is notified that it must collect the remaining amount due for the medical product or service from the cardholder.

In operation, the system can operate rapidly to provide a transaction which is essentially accomplished in real time even though there are a plurality of entities involved in each transaction. The perception to both the cardholder and the medical product or service provider is that there is a single transaction which results either in the entire cost of the medical product or service being paid or in the requirement that the cardholder must pay some or all of the cost of the medical product or service at that time. Optionally, the healthcare debit card may also function as a conventional charge card (credit or debit) as well for use in transactions other than for the purchase of medical products or services. In this case, the healthcare debit card can also be the non-healthcare-related financial account if desired.

In the preferred embodiment, the system administrator is the interface between the other entities in the system of the present invention. Thus, the flow of information passes through the system administrator, thereby enabling the system administrator to ascertain the status of each transaction. Optionally, the system administrator's role can be reduced, but those skilled in the art will recognize that one of the entities in the system serves to route the various operations to ensure that they are all carried out in the proper order.

It may therefore be seen that the present invention teaches a system and method for linking a healthcare debit card to both a healthcare-related financial account and a non-healthcare-related financial account in addition to linking the healthcare debit card to a medical insurance program. The healthcare debit card used in the system and method of the present invention contains sufficient information, either in printed form or in electronic form or in both forms, to enable medical product and service providers to ascertain that the healthcare debit card provides for payment from the three sources. The system and method of the present invention is capable of working which any of a plurality of different healthcare-related financial accounts, including FSA, HSA, and HRA healthcare-related financial accounts.

The system and method of the present invention provide coordination between the submissions for payment of medical products and services to a medical insurance provider, the healthcare-related financial account, and the non-healthcare-related financial account to ensure that the submissions to these three entities are made quickly and in the proper sequence. The system and method of the present invention are capable of operation in real time or in near-real time, thereby enabling complete resolution of payment for the medical products and services at the time of delivery. The healthcare debit card used in the system and method of the present invention can optionally be used as a conventional credit or debit card for use in purchasing non-medical products and services.

The system and method of the present invention are flexible of design and robust in operation, and once established the system requires little or no effort to maintain it other than to keep the employee or cardholder data current. The system of the present invention is also relatively inexpensive to implement and to operate to give it a high perceived value-to-cost ratio to enhance its market appeal and to thereby afford it the broadest possible market. Finally, all of the aforesaid advantages and objectives of the system and method of the present invention are achieved without incurring any substantial relative disadvantage.

DESCRIPTION OF THE DRAWINGS

These and other advantages of the present invention are best understood with reference to the drawings, in which:

FIG. 1 is a front side plan view of a healthcare debit card which may be linked to healthcare-related and non-healthcare-related financial accounts;

FIG. 2 is a back side plan view of the healthcare debit card illustrated in FIG. 1;

FIG. 4 is a flow diagram showing the process used to add, delete, or change employee or cardholder users of the system illustrated in FIG. 3;

FIG. 5 is a flow diagram showing exemplary uses of the healthcare debit card illustrated in FIGS. 1 and 2 in the system illustrated in FIG. 3;

FIG. 6 is a flow diagram showing further exemplary uses of the healthcare debit card illustrated in FIGS. 1 and 2 in the system illustrated in FIG. 3; and FIG. 7 is a flow diagram showing still further exemplary uses of the healthcare debit card illustrated in FIGS. 1 and 2 in the system illustrated in FIG. 3.

DETAILED DESCRIPTION OF THE PREFERRED EMBODIMENT

Figure 3:
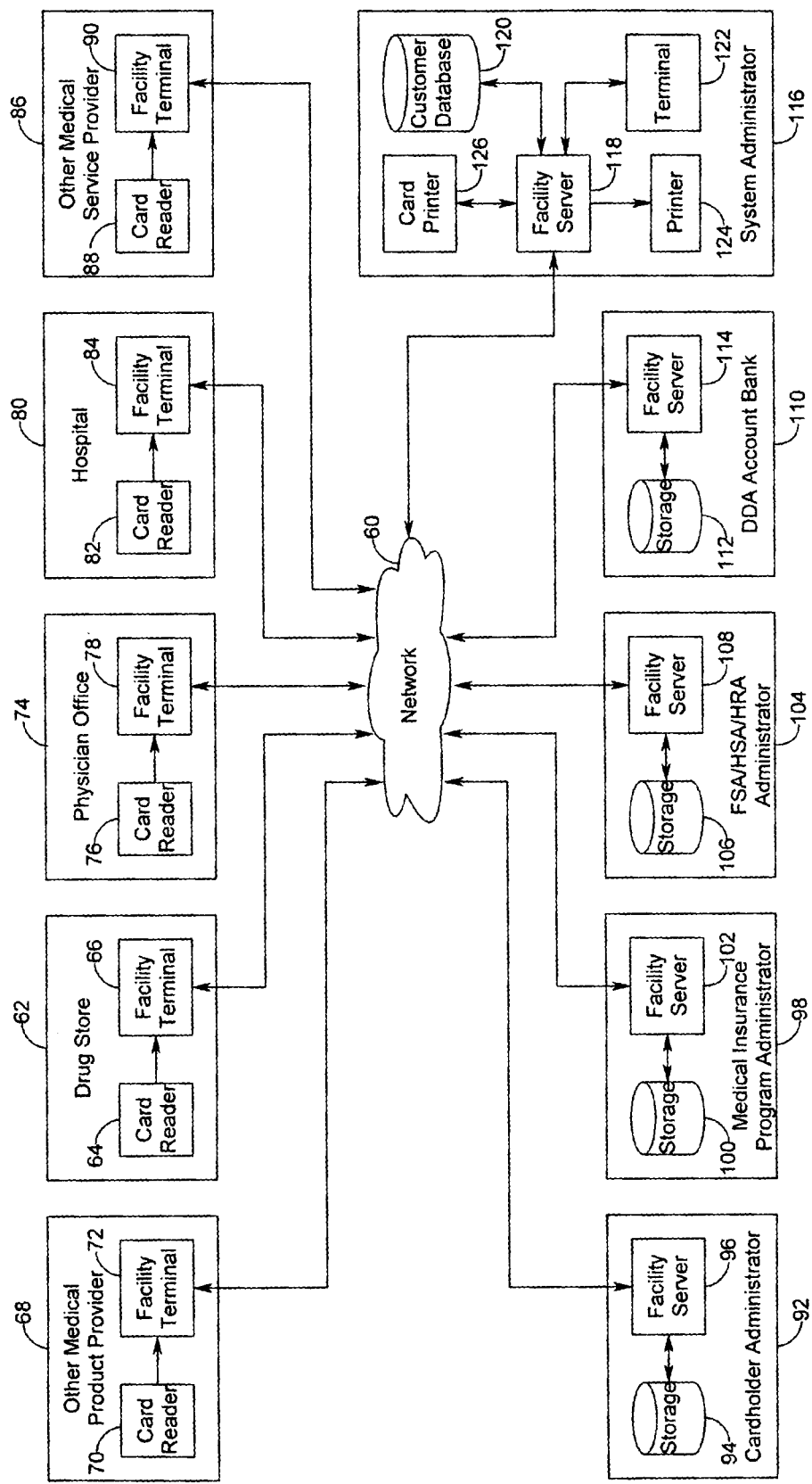
FIG. 3 is a functional schematic diagram of a system for linking the healthcare debit card illustrated in FIGS. 1 and 2 to a medical insurance provider and to healthcare-related and non-healthcare-related financial accounts each of which may be used to pay for medical services and products.

The preferred embodiment of the present invention utilizes a healthcare debit card 20 which is illustrated in FIGS. 1 and 2. The healthcare debit card 20, which includes a front side as shown in FIG. 1 and a rear side as shown in FIG. 2, is preferably made of plastic material as is conventional. Referring first to the front side of the healthcare debit card 20 as shown in FIG. 1, a medical insurance provider name 22 is prominently located near the top of the healthcare debit card 20. A cardholder name 24 is located near the bottom of the healthcare debit card 20.

Prominently located on the healthcare debit card 20 is a healthcare debit card number 26, and below the healthcare debit card number 26 near the left side of the healthcare debit card 20 is a four digit verification number 28. Located above the cardholder name 24 and below the healthcare debit card number 26 is a healthcare debit card expiration date 30. Located just to the right of the healthcare debit card expiration date 30 is a financial network symbol 32, which may be used to identify a financial network which may be used to facilitate part of the payment process, as will become apparent later in conjunction with a description of the operation of the system and method for linking the healthcare debit card 20 to healthcare-related and non-healthcare-related financial accounts of the present invention. In the preferred embodiment, the cardholder name 24, the healthcare debit card number 26, the healthcare debit card expiration date 30, and 32 are all both printed and embossed on the healthcare debit card 20.

Also located on the healthcare debit card 20 is healthcare plan information indicated generally by the reference numeral 34. The healthcare plan information 34 may include, for example, a subscriber identification number, the effective date of the healthcare plan, the healthcare plan group name, the healthcare plan group identification number, and the copay amounts which are required for various medical services under the healthcare plan. Located near the right side of the healthcare debit card 20 is a holographic logo 36, and located below the holographic logo 36 is a financial network logo 38, which may be used to identify the financial network which is used to facilitate part of the payment process.

Referring now to the back side of the healthcare debit card 20 shown in FIG. 2, a magnetic stripe 40 is located across the healthcare debit card 20 near the top thereof. The magnetic stripe 40 may be used to store information about the card, the cardholder, the healthcare plan, and financial account information as well. Located below the magnetic stripe 40 is a cardholder signature area 42, where the cardholder typically must sign the healthcare debit card 20 in order for the healthcare debit card 20 to be valid.

Located on the left side of the healthcare debit card 20 is healthcare plan service information 44, which can include telephone numbers, an Internet address, and a mailing address used by the healthcare plan. Located below the healthcare plan service information 44 is healthcare financial account service information 46, which may be used to provide telephone numbers and an Internet address for the administrator of a healthcare financial account such as an FSA/HSA/HRA financial account. Located near the bottom of the healthcare debit card 20 is healthcare service information 48 relating to specific services which may be provided by the healthcare plan service provider.

Located on the healthcare debit card 20 below the cardholder signature area 42 is additional healthcare plan information 50, which may include, for example, information relating to the healthcare plan system administrator, terms and conditions governing the use of the healthcare debit card 20, and information relating to the financial network which is used to facilitate part of the payment process. Located below the additional healthcare plan information 50 are a medical network logo 52 and a healthcare plan provider logo 54, which may respectively be used to identify a health maintenance organization ("HMO") and/or the healthcare provider.

Instead of or in addition to the magnetic stripe 40 located across the healthcare debit card 20 near the top thereof, a smart chip 56 may be embedded into the healthcare debit card 20 as shown in FIG. 1. The smart chip 56 may be used to store information about the card, the cardholder, the healthcare plan, and financial account information as well. The smart chip 56 may typically be a thin and flat integrated circuit assembly which includes a microprocessor and memory. When the healthcare debit card 20 containing the smart chip 56 is inserted into a reader (not shown), it wirelessly transfers data to and from the reader via radio frequency ("RF"). The smart chip 56 needs no internal power source since it is powered by the signal from the reader.

An integrated circuit assembly suitable for use as the smart chip 56 is disclosed in U.S. Pat. No. 5,600,175, and the operation of a transponder circuit contained in the smart chip 56 is disclosed in U.S. Pat. No. 5,053,774. Both U.S. Pat. Nos. 5,600,175 and 5,053,774 are hereby incorporated herein by reference in their entirety. A healthcare debit card 20 containing the smart chip 56 is more secure than if only the magnetic stripe 40 was used. The smart chip 56 can be programmed to self-destruct if the wrong password is entered too many times.

Referring next to FIG. 3, a system for using the healthcare debit card 20 (illustrated in FIGS. 1 and 2) to establish payment to medical service and/or product providers from a healthcare-related financial account and a non-healthcare-related financial account is illustrated. While in FIG. 3 all of the entities shown are depicted as being connected with a single network 60, it will be understood by those skilled in the art that multiple networks may be used instead, and that some or all of these networks may be private, dedicated networks in addition to (or instead of) the use of public networks such as the Internet.

The healthcare debit card 20 can be made of a variety of different materials, including conventional PVC stock with an integrated magnetic stripe 40, a plastic-laminated paper or cardstock with an integrated magnetic stripe 40, PVC with an integrated smart chip 56 (the smart chip 56 having the same information which would otherwise have been included in a magnetic stripe 40), or PVC with both an integrated magnetic stripe 40 and an integrated smart chip 56.

FIG. 3 depicts two medical product providers and three medical service providers, all of which are connected to the network 60. These five medical product and medical service providers are typical of the types of providers which may be accommodated by the system and method for linking a healthcare debit card to healthcare-related and non-healthcare-related financial accounts of the present invention. A drug store 62 which is a provider of such medical products as prescription drugs, nonprescription drugs and supplements, and other medical goods has a card reader 64 which is connected to a facility terminal 66, which in turn is connected to the network 60. A provider of other medical products 68 has a card reader 70 which is connected to a facility terminal 72, which in turn is connected to the network 60.

A physician office 74 which is most typically a provider of medical services has a card reader 76 which is connected to a facility terminal 78, which in turn is connected to the network 60. A hospital 80 which is also predominantly a provider of medical services has a card reader 82 which is connected to a facility terminal 84, which in turn is connected to the network 60. A provider of other medical services 86 which may be a provider of medical services such as chiropractic services, various types of physical therapy, or mental health services has a card reader 88 which is connected to a facility terminal 90, which in turn is connected to the network 60.

It may be noted in passing that the card readers 64, 70, 76, 82, and 88 can each be either or both of a magnetic stripe reader or a smart chip reader. The facility terminals 66, 72, 78, 84, and 90 in conjunction with the card readers 64, 70, 76, 82, and 88 can be personal computers having wedge reader/pin pads connected thereto, Internet-enabled point-of-sale terminals, or Internet-enabled retail cash register/sales systems with an integrated or stand alone card reader/pin pad.

FIG. 3 also depicts three administrators which are connected to the network 60, each of which administrators is a key player in the operation of typical healthcare systems. A cardholder administrator 92 that enrolls employees or other cardholders serviced by a particular healthcare program has a storage medium 94 which is connected to a facility server 96, which in turn is connected to the network 60. The storage medium 94 is used to store data regarding the employees or other cardholders.

A medical insurance program administrator 98 which administers the healthcare program (typically having defined healthcare benefits, payment costs, and preferred providers with which it has fee agreements) has a storage medium 100 which is connected to a facility server 102, which in turn is connected to the network 60. The storage medium 100 is used to store data regarding the medical insurance program, including eligibility information, coverage information, and copay amounts. A healthcare-related financial account administrator 104 which administers employee or cardholder healthcare financial accounts (such as FSA, HAS, and HRA accounts) has a storage medium 106 which is connected to a facility server 108, which in turn is connected to the network 60. The storage medium 106 is used to store data regarding the healthcare-related financial accounts, including eligibility information and account balances.

FIG. 3 also shows two other entities which are included in the system and method for linking a healthcare debit card to healthcare-related and non-healthcare-related financial accounts of the present invention, the first of which is a DDA deposit bank 110 having a non-healthcare-related financial account which belongs to the employee or cardholder. The employee or cardholder's account at the DDA deposit bank 110 can be a checking account, a savings account, or a credit card account, and need not be a dedicated account which is used only by the system and method for linking a healthcare debit card to healthcare-related and non-healthcare-related financial accounts. The DDA deposit bank 110 has a storage medium 112 which is connected to a facility server 114, which in turn is connected to the network 60. The storage medium 112 is used to store data regarding the non-healthcare-related financial accounts, including personal identification numbers ("PIN's") and account balances.

While the non-healthcare-related financial accounts used by the system and method for linking a healthcare debit card to healthcare-related and non-healthcare-related financial accounts of the present invention are preferably DDA deposit accounts such as checking or savings accounts, they could also be any of debit accounts, a dynamic lines of credit, revolving lines of credit, gift card financial accounts (including incentive-based accounts), and HSA investment accounts. Additionally, there could be more than one healthcare-related financial account and/or more than one non-healthcare-related financial account associated with a single healthcare debit card 20. Theoretically there could be a relatively large number of financial accounts associated with a single healthcare debit card 20, with the system of the present invention being capable of handling at least twenty different financial accounts associated with a single healthcare debit card 20.

The remaining entity shown in FIG. 3 is a system administrator 116 which is the heart of the system for linking a healthcare debit card to healthcare-related and non-healthcare-related financial accounts of the present invention, since the system administrator 116 functions to coordinate communications from and between all of the other entities shown in FIG. 3. The system administrator 116 has a facility server 118 which is connected to the network 60. The facility server 118 accesses a customer database 120 in which information relating to the system of the present invention is stored. A terminal 122 is connected to the facility server 118, and a printer 124 and a card printer 126 are used to respectively provide paper communications regarding the system of the present invention and cards which may be used by employees or cardholders having a healthcare program administered by the system of the present invention.

Referring now to FIG. 4, a process which may be used to add, delete, or change employees or cardholders participating in the system for linking a healthcare debit card to healthcare-related and non-healthcare-related financial accounts of the present invention is illustrated. The process begins at a process initiation step 130 in which the cardholder administrator 92 (illustrated in FIG. 3) provides information to the system administrator 116 (also illustrated in FIG. 3) relating to the addition or deletion of an employee or cardholder, or relevant updated data regarding an employee or cardholder.

The process then moves to a new employee determination step 132 in which it is determined whether or not the information provided by the cardholder administrator 92 is for a new employee or cardholder. If the information is for a new employee or cardholder, the process moves to an add employee to database and print card step 134 where the data regarding the employee or cardholder is added to the database contained in the customer database 120 (illustrated in FIG. 3) and a healthcare debit card 20 (illustrated in FIGS. 1 and 2) is printed and mailed to the new employee or cardholder. If, on the other hand, the information is not for a new employee or cardholder, the process moves instead to a delete employee determination step 136.

In the delete employee determination step 136, it is determined whether or not the information provided by the cardholder administrator 92 is for an employee or cardholder who is to be deleted from the system of the present invention. If the information is for an employee or cardholder to be deleted from the system, the process moves to a delete employee from database step 138 where the specified employee or cardholder is deleted from the database contained in the customer database 120. If, on the other hand, the information is not for an employee or cardholder to be deleted from the system, the process moves instead to a change employee information determination step 140.

In the change employee information determination step 140, it is determined whether or not the information provided by the cardholder administrator 92 is a change in information regarding an employee or cardholder participating in the system of the present invention. If the information is a change in information for an employee or cardholder participating in the system, the process moves to a change employee information step 142 where the information regarding the employee or cardholder is updated in the database contained in the customer database 120. If, on the other hand, the information is not for a change in information for an employee or cardholder participating in the system, the process moves instead to manual review step 144 where the information is manually reviewed by a service employee who takes appropriate action as necessary.

Referring next to FIGS. 5 through 7, a flow diagram which shows by way of example the operation of the system for linking a healthcare debit card to healthcare-related and non-healthcare-related financial accounts of the present invention is illustrated. Referring first primarily to FIG. 5, the operation of the system begins with the employee or cardholder using the healthcare debit card 20 (illustrated in FIGS. 1 and 2) to purchase a medical product or service. With regard first to the purchase of a medical product from a medical product provider 150 which may be a drug store or some other medical product provider, the process begins with the employee or cardholder purchasing a medical product in a cardholder purchases medical product step 152.

At the time of purchase of the medical product, the employee or cardholder presents the healthcare debit card 20 to an employee of the medical product provider 150 in a cardholder presents card step 154. The employee of the medical product provider 150 then either scans the card with a card reader or manually enters the healthcare debit card number 26 (illustrated in FIG. 1) using a terminal in a scan card or enter card number step 156. Optionally, the system of the present invention may require the employee's or cardholder's personal identification number (a "PIN") which is associated with the healthcare debit card 20. If it does, the employee or cardholder enters the PIN in a cardholder enters PIN number step 158.

Following this step, the medical product information (which is typically derived by scanning code on the medical product or by manually entering information regarding the medical product), the healthcare debit card number 26, and the employee's or cardholder's PIN (optional) are transmitted in a transmit information step 160 to a system administrator 162, where the transmitted data is received in a receive information step 164.

A similar process is followed by the employee or cardholder to use the healthcare debit card 20 to purchase a medical service (or a medical product) from a medical service provider 166 which may be a physician's office, a hospital, or some other medical service provider. This process begins with the employee or cardholder receiving a medical service (or a medical product) in a cardholder receives medical service step 168. In consideration for the receipt of the medical service (or a medical product), the employee or cardholder presents the healthcare debit card 20 in a cardholder presents card step 170. The employee of the medical service provider 166 then either scans the card through a card reader or manually enters the healthcare debit card number 26 in a scan card or enter card number step 172.

Optionally, the system of the present invention may require the employee's or cardholder's personal identification number (a "PIN") which is associated with the healthcare debit card 20. If it does, the employee or cardholder enters the PIN in a cardholder enters PIN number step 174. Following this step, the medical service (or medical product) information (which is typically derived by manually entering information regarding the medical service), the healthcare debit card number 26, and the employee's or cardholder's PIN are transmitted in a transmit information step 176 to the system administrator 162, where the transmitted data is received in the receive information step 164.

For either a medical product or a medical service, following the receive information step 164 the process then moves to a send claim information step 178 in which the medical product or service information, the healthcare debit card number 26, and the employee's or cardholder's PIN (optional) are provided to the medical insurance program administrator 180. The medical insurance program administrator 180 analyzes the medical product or service information, the healthcare debit card number 26, and the employee's or cardholder's PIN (optional) in a product or service coverage determination step 182.

If it is determined in the product or service coverage determination step 182 that the medical product or service is covered by the employee's or cardholder's medical insurance, the process moves to a pay claim for product or service step 184 where the medical insurance program administrator 180 pays the appropriate amount for the medical product or service. In addition, the pay claim for product or service step 184 also provides information regarding any amounts which will be written off by the provider, and the remaining amount which is due for the medical product or service to the system administrator 162, where this information is received in a receive claim coverage information step 186.

If, on the other hand, it is determined in the product or service coverage determination step 182 that the medical product or service is not covered by the employee's or cardholder's medical insurance, information indicating that the medical product or service is not covered by the employee's or cardholder's medical insurance (as well as information regarding any amounts which will be written off by the provider pursuant to contract) is provided to the system administrator 162, where this information is received in the receive claim coverage information step 186.

Referring primarily now to FIG. 6, from the receive claim coverage information step 186, the process next moves to a send unpaid claim information step 188 in which information relating to the remaining amount which is due for the medical product or service is forwarded to a healthcare-related financial account administrator 190. At the healthcare-related financial account administrator 190, a determination is made as to whether the medical product or service is a covered medical product or service in a coverage determination step 192. If it is determined in the coverage determination step 192 that the medical product or service is covered by the employee's or cardholder's healthcare-related financial account, the process moves to an account fund sufficiency determination step 194.

In the account fund sufficiency determination step 194, it is determined whether or not there are sufficient funds in the employee's or cardholder's healthcare-related financial account to pay the remaining amount which is due for the medical product or service. If there are sufficient funds (or if the financial account can advance funds), the process moves to a pay balance for product or service step 196 where the coverage determination step 192 pays the remaining amount which is due for the medical product or service to the provider of the medical product or service. The process them moves to a receive payment information step 198 where the system administrator 162 is provided with information from the healthcare-related financial account administrator 190 which indicates that the remaining amount which is due for the medical product or service has been paid. In this event, the process then terminates in a transaction complete step 200.

If, on the other hand, it is determined in the account fund sufficiency determination step 194 that there are not sufficient funds in the employee's or cardholder's healthcare-related financial account to pay the remaining amount which is due for the medical product or service, the process moves instead to a pay remaining funds to provider step 202. In the pay remaining funds to provider step 202, the remaining funds (if any) in the employee's or cardholder's healthcare-related financial account are paid to the provider of the medical product or service. The process them moves to a receive amount due information step 204 where the system administrator 162 is provided with information from the healthcare-related financial account administrator 190 which indicates the remaining amount which is due for the medical product or service.

Returning now to the coverage determination step 192, if on the other hand it is determined that the medical product or service is not covered by the employee's or cardholder's healthcare-related financial account, the process moves instead directly to the receive amount due information step 204, where the system administrator 162 is informed that the medical product or service is not covered and of the remaining amount which is due for the medical product or service. Thus, the process will include the receive amount due information step 204 whenever there is a remaining amount which is due for the medical product or service. It is from the receive amount due information step 204 where the system and method for linking a healthcare debit card to healthcare-related and non-healthcare-related financial accounts of the present invention are focused.

As previously mentioned, it is possible to have more than one healthcare-related financial account associated with a healthcare debit card 20. If there is more than one healthcare-related financial account associated with a healthcare debit card 20, they will be sequentially accessed by the system administrator 116 to determine coverage and the availability of funds in each account. Thus, the coverage determination step 192, the account fund sufficiency determination step 194, and the pay balance for product or service step 196 or the pay remaining funds to provider step 202 will be performed in conjunction with each healthcare-related financial account administrator 190 until the healthcare-related financial accounts associated with a healthcare debit card 20 have been exhausted.

Referring primarily now to FIG. 7, from the receive amount due information step 204, the process moves to a send amount due information to DDA account bank step 206 in which information relating to the remaining amount which is due for the medical product or service is forwarded to a non-healthcare-related financial account administrator 208. The non-healthcare-related financial account administrator 208 is typically a bank or other financial institution, and the non-healthcare-related financial account may be either a conventional savings account, a checking account, or a credit card account at the bank (it need not be a special or dedicated financial account). The send amount due information to DDA account bank step 206 also forwards information held by the system administrator 162 relating to the account number of the employee's or cardholder's account at the non-healthcare-related financial account administrator 208, as well as the PIN for the financial account.

A determination is made by the non-healthcare-related financial account administrator 208 as to whether the information provided from the system administrator 162 identifies a valid financial account and includes all of the information required to perform a financial transaction from that financial account in a account authorization determination step 210. If it is determined in the account authorization determination step 210 that the account authorization information is not valid, the system administrator 162 is informed in a receive failure to pay notification step 212. Following such a notification, the process moves to a notify product or service provider to collect from cardholder step 214, where the provider is notified of the remaining amount which is due for the medical product or service. In this event, the process then terminates in a transaction complete step 216.

If, on the other hand, it is determined in the account authorization determination step 210 that the account authorization information is valid, the process moves instead to a sufficient funds in account determination step 218. If it determined in the sufficient funds in the account determination step 218 that there are insufficient funds in the non-healthcare-related financial account, the system administrator 162 is informed in the receive failure to pay notification step 212. In this event, the process then again moves to the notify product or service provider to collect from cardholder step 214 and the transaction complete step 216.

If, on the other hand, it is determined in the sufficient funds in account determination step 218 that there are sufficient funds in the non-healthcare-related financial account to pay the remaining amount which is due for the medical product or service, the process moves to a pay balance for product or service step 220. In the pay balance for product or service step 220, the non-healthcare-related financial account administrator 208 pays the remaining amount which is due for the medical product or service to the system administrator 162. The process them moves to a receive payment information step 222 where the system administrator 162 is provided with information from the non-healthcare-related financial account administrator 208 which indicates that the remaining amount which is due for the medical product or service has been paid to the system administrator 162.

As previously mentioned, it is possible to have more than one non-healthcare-related financial account associated with a healthcare debit card 20. If there is more than one non-healthcare-related financial account associated with a healthcare debit card 20, they will be sequentially accessed by the system administrator 116 to determine the availability of funds in each account. Thus, the account authorization determination step 210 and the sufficient funds in account determination step 218 or the pay balance for product or service step 220 will be performed in conjunction with each non-healthcare-related financial account administrator 208 until the non-healthcare-related financial accounts associated with a healthcare debit card 20 have been exhausted.

Following an indication that the remaining amount which is due for the medical product or service has been paid to the system administrator 162, the process then moves to a transfer funds to provider step 224 in which the system administrator 162 transfers the remaining amount which is due for the medical product or service to the medical product or service provider. Next, in a notify provider of payment step 226, the system administrator 162 notifies the medical product or service provider that the remaining amount which was due for the medical product or service has been paid. Finally, the process terminates in a transaction complete step 228.

It may therefore be appreciated from the above detailed description of the preferred embodiment of the present invention that it teaches a system and method for linking a healthcare debit card to both a healthcare-related financial account and a non-healthcare-related financial account in addition to linking the healthcare debit card to a medical insurance program. The healthcare debit card used in the system and method of the present invention contains sufficient information, either in printed form or in electronic form or in both forms, to enable medical product and service providers to ascertain that the healthcare debit card provides for payment from the three sources. The system and method of the present invention is capable of working which any of a plurality of different healthcare-related financial accounts, including FSA, HSA, and HRA healthcare-related financial accounts.

The system and method of the present invention provide coordination between the submissions for payment of medical products and services to a medical insurance provider, the healthcare-related financial account, and the non-healthcare-related financial account to ensure that the submissions to these three entities are made quickly and in the proper sequence. The system and method of the present invention are capable of operation in real time or in near-real time, thereby enabling complete resolution of payment for the medical products and services at the time of delivery. The healthcare debit card used in the system and method of the present invention can optionally be used as a conventional credit or debit card for use in purchasing non-medical products and services.

The system and method of the present invention are flexible of design and robust in operation, and once established the system requires little or no effort to maintain it other than to keep the employee or cardholder data current. The system of the present invention is also relatively inexpensive to implement and to operate to give it a high perceived value-to-cost ratio to enhance its market appeal and to thereby afford it the broadest possible market. Finally, all of the aforesaid advantages and objectives of the system and method of the present invention are achieved without incurring any substantial relative disadvantage.

Although the foregoing description of the system and method of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A system, comprising:
a data processing system located remote from a terminal device, the data processing system comprising a system interface, memory, and one or more processors to:
receive, via a network from the terminal device, an indication to process an electronic transaction as a single electronic transaction at the terminal device corresponding to a series of electronic transactions performed by the data processing system via: i) one or more links established with a plurality of remote devices comprising at least one of a cardholder administrator device, a medical insurance program administrator device, a healthcare financial account administrator device, or a financial institution device; and ii) data including at least one of healthcare financial account information, non-healthcare-related financial account information, or insurance provider information;
determine, responsive to the indication to process the electronic transaction, that the electronic transaction is authorized using an insurance policy associated with the insurance provider information corresponding to the electronic transaction;
cause, responsive to the determination that the electronic transaction is authorized using the insurance policy, a transfer of funds corresponding to the insurance policy of the insurance provider information from the data;
determine that the electronic transaction is at least partially authorized using a healthcare-related policy provided by the healthcare financial account information;
generate, responsive to the determination that the electronic transaction is at least partially authorized using the healthcare-related policy and the insurance policy, a first request to access funds from a healthcare financial account corresponding to the healthcare financial account information from the data;
determine that an amount of funds in the healthcare financial account is below a threshold;
transmit, via the one or more links established to process the electronic transaction as the single electronic transaction corresponding to the series of electronic transactions and responsive to the determination that the amount of funds is below the threshold, a second request to access a remaining portion of funds from a non-healthcare-related financial account corresponding to the non-healthcare-related financial account information; and
provide, via the network responsive to execution of the electronic transaction as the series of electronic transactions comprising the first request and the second request, an indication of completion of the electronic transaction.

2. The system of claim 1, comprising:
the data processing system to establish, via the network, the one or more links with the plurality of remote devices.

3. The system of claim 1, comprising:
the data processing system to split, responsive to the determination that the amount of funds is below the threshold, the electronic transaction into the series of electronic transactions comprising the first request and the second request.

4. The system of claim 3, comprising:
the data processing system to reduce, based on the insurance policy or the healthcare-related policy and prior to the split of the electronic transaction into the first request and the second request, an amount of the electronic transaction.

5. The system of claim 1, comprising:
the data processing system to provide the indication of the completion of the electronic transaction to the terminal device via the network.

6. The system of claim 1, comprising:
the data processing system to receive, from the terminal device, an indication to process the electronic transaction as the series of electronic transactions at the data processing system using the data.

7. The system of claim 1, wherein the terminal device connects to an electronic card reader device configured to interface with at least one of a magnetic stripe configured by a printer or a radio frequency communication device to receive, from at least one of the magnetic stripe configured by the printer or the radio frequency communication device, the healthcare financial account information, the non-healthcare-related financial account information, and the insurance provider information.

8. The system of claim 7, wherein at least one of the magnetic stripe configured by the printer or the radio frequency communication device comprises information about at least one of a card number, cardholder information, the insurance provider information, or information regarding copay amounts.

9. The system of claim 1, comprising the data processing system to:
identify, for the electronic transaction, the insurance policy or the healthcare-related policy comprising at least one of an authorization process, validation process, or a resource availability process;
determine, based on the insurance policy or the healthcare-related policy, that a first portion of the electronic transaction is authorized and a second portion of the electronic transaction fails authorization; and
split the electronic transaction into a third request for the second portion that fails authorization.

10. The system of claim 9, comprising:
the data processing system to transmit the third request to at least one of the terminal device or a third-party server remote from the data processing system.

11. A method, comprising:
receiving, by a data processing system comprising a system interface, memory, and one or more processors, via a network from a terminal device located remote from the data processing system, an indication to process an electronic transaction as a single electronic transaction at the terminal device corresponding to a series of electronic transactions performed by the data processing system via: i) one or more links established with a plurality of remote devices comprising at least one of a cardholder administrator device, a medical insurance program administrator device, a healthcare financial account administrator device, or a financial institution device; and ii) data including at least one of healthcare financial account information, non-healthcare-related financial account information, or insurance provider information;
determining, by the data processing system responsive to the indication to process the electronic transaction, that the electronic transaction is authorized using an insurance policy associated with the insurance provider information corresponding to the electronic transaction;
causing, by the data processing system responsive to the determination that the electronic transaction is authorized using the insurance policy, a transfer of funds corresponding to the insurance policy of the insurance provider information from the data;
determining, by the data processing system, that the electronic transaction is at least partially authorized using a healthcare-related policy provided by the healthcare financial account information;
generating, by the data processing system responsive to the determination that the electronic transaction is at least partially authorized using the healthcare-related policy and the insurance policy, a first request to access funds from a healthcare financial account corresponding to the healthcare financial account information from the data;
determining, by the data processing system, that an amount of funds in the healthcare financial account is below a threshold;
transmitting, by the data processing system via the one or more links established to process the electronic transaction as the single electronic transaction corresponding to the series of electronic transactions and responsive to the determination that the amount of funds is below the threshold, a second request to access a remaining portion of funds from a non-healthcare-related financial account corresponding to the non-healthcare-related financial account information; and
providing, by the data processing system via the network responsive to execution of the electronic transaction as the series of electronic transactions comprising the first request and the second request, an indication of completion of the electronic transaction.

12. The method of claim 11, comprising:
establishing, by the data processing system via the network, the one or more links with the plurality of remote devices.

13. The method of claim 11, comprising:
splitting, by the data processing system responsive to the determination that the amount of funds is below the threshold, the electronic transaction into the series of electronic transactions comprising the first request and the second request.

14. The method of claim 13, comprising:
reducing, by the data processing system based on the insurance policy or the healthcare-related policy and prior to the split of the electronic transaction into the first request and the second request, an amount of the electronic transaction.

15. The method of claim 11, comprising:
providing, by the data processing system, the indication of the completion of the electronic transaction to the terminal device via the network.

16. The method of claim 11, comprising:
receiving, by the data processing system from the terminal device, an indication to process the electronic transaction as the series of electronic transactions at the data processing system using the data.

17. The method of claim 11, wherein the terminal device connects to an electronic card reader device configured to interface with at least one of a magnetic stripe configured by a printer or a radio frequency communication device to receive, from at least one of the magnetic stripe configured by the printer or the radio frequency communication device, the healthcare financial account information, the non-healthcare-related financial account information, and the insurance provider information.

18. The method of claim 17, wherein at least one of the magnetic stripe configured by the printer or the radio frequency communication device comprises information about at least one of a card number, cardholder information, the insurance provider information, or information regarding copay amounts.

19. The method of claim 11, comprising:
identifying, by the data processing system for the electronic transaction, the insurance policy or the healthcare-related policy comprising at least one of an authorization process, validation process, or a resource availability process;
determining, by the data processing system based on the insurance policy or the healthcare-related policy, that a first portion of the electronic transaction is authorized and a second portion of the electronic transaction fails authorization; and
splitting, by the data processing system, the electronic transaction into a third request for the second portion that fails authorization.

20. The method of claim 19, comprising:
transmitting, by the data processing system, the third request to at least one of the terminal device or a third-party server remote from the data processing system.

* * * * *